(12) United States Patent
Lees et al.

(10) Patent No.: US 12,089,970 B2
(45) Date of Patent: *Sep. 17, 2024

(54) SURGICAL STRINGER AND METHODS OF MANUFACTURING AND USING SAME

(71) Applicant: Artisan Medical Devices Corp., Medford, NJ (US)

(72) Inventors: John Lees, Medford, NJ (US); James J. Lees, Medford, NJ (US)

(73) Assignee: Artisan Medical Devices Corp., Medford, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/312,980

(22) Filed: May 5, 2023

(65) Prior Publication Data

US 2023/0270516 A1   Aug. 31, 2023

Related U.S. Application Data

(63) Continuation of application No. 16/370,931, filed on Mar. 30, 2019, now Pat. No. 11,678,949.

(51) Int. Cl.
*A61B 50/20* (2016.01)
*A47F 5/01* (2006.01)
*B65B 5/08* (2006.01)
*F16M 11/22* (2006.01)

(52) U.S. Cl.
CPC ............ *A61B 50/20* (2016.02); *F16M 11/22* (2013.01); *A47F 5/01* (2013.01); *B65B 5/08* (2013.01); *F16M 2200/08* (2013.01)

(58) Field of Classification Search
CPC ......... A61B 50/00; A61B 50/20; A61B 50/22; A61B 50/24; A61B 50/33; A61B 2050/0075; B65B 5/08; F16M 11/22; F16M 2200/08

See application file for complete search history.

(56) References Cited

U.S. PATENT DOCUMENTS

| | | | | |
|---|---|---|---|---|
| 1,005,820 A * | 10/1911 | Essex | ......................... | A47F 5/01 211/49.1 |
| 1,008,477 A * | 11/1911 | Kohn | ......................... | A47F 7/24 211/182 |
| 1,150,109 A * | 8/1915 | Flanders | .................... | A47F 5/01 211/49.1 |
| 4,021,211 A * | 5/1977 | Turek | .................. | B01D 53/0454 95/11 |
| 11,678,949 B2 * | 6/2023 | Lees | ....................... | F16M 11/22 269/74 |
| 2004/0050814 A1 * | 3/2004 | Roush | ................... | A47F 5/0018 211/187 |

FOREIGN PATENT DOCUMENTS

WO   WO-2014124265 A1 *   8/2014   ............. A61B 50/20

* cited by examiner

*Primary Examiner* — Tan Le
(74) *Attorney, Agent, or Firm* — SLEMAN & LUND LLP

(57) ABSTRACT

A surgical stringer includes a pair of bases, each of the pair of bases having a flat bottom surface, the pair of bases being rotatable with respect to one another, and a pair of poles, each of the pair of poles being coupled to a one of the pair of bases and extending orthogonally thereto, the distance between the pair of poles being variable.

19 Claims, 3 Drawing Sheets

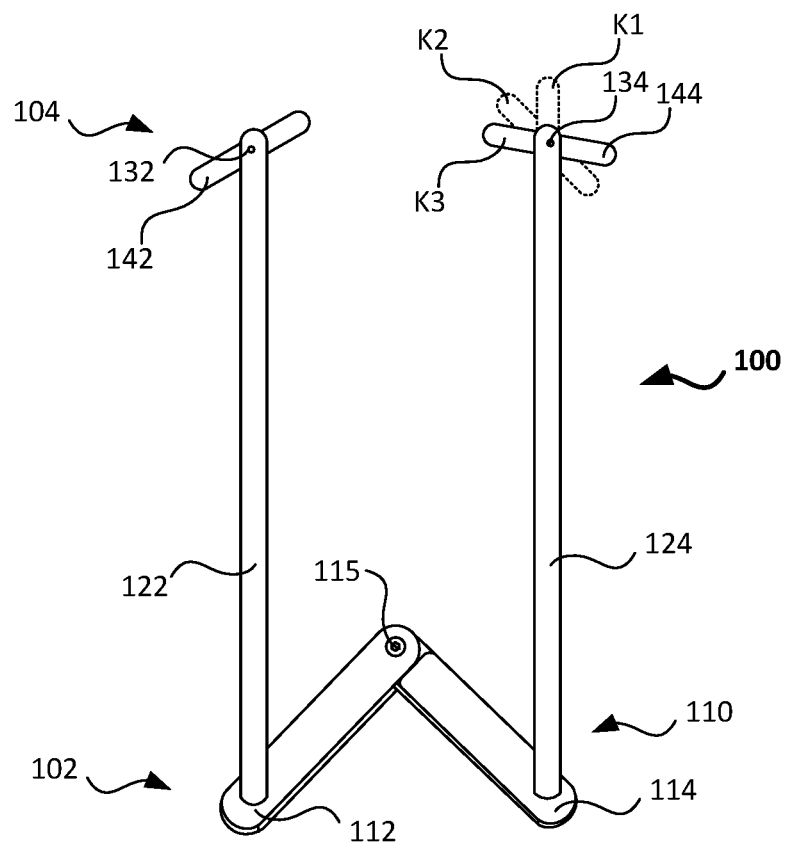
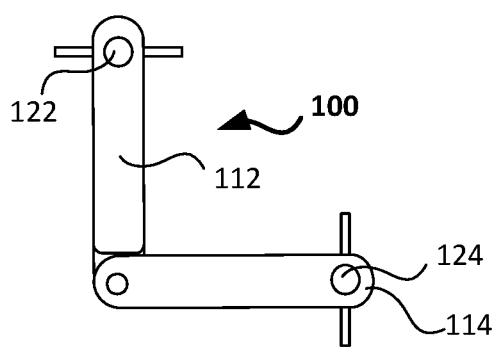
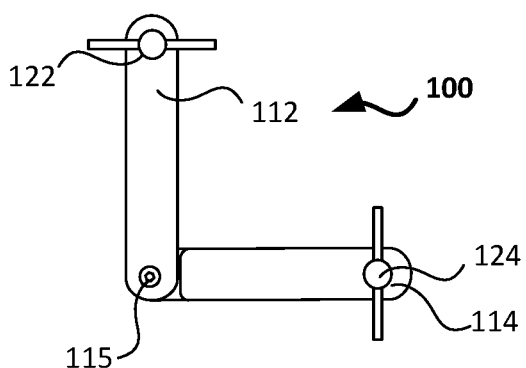
FIG. 1
FIG. 2
FIG. 3

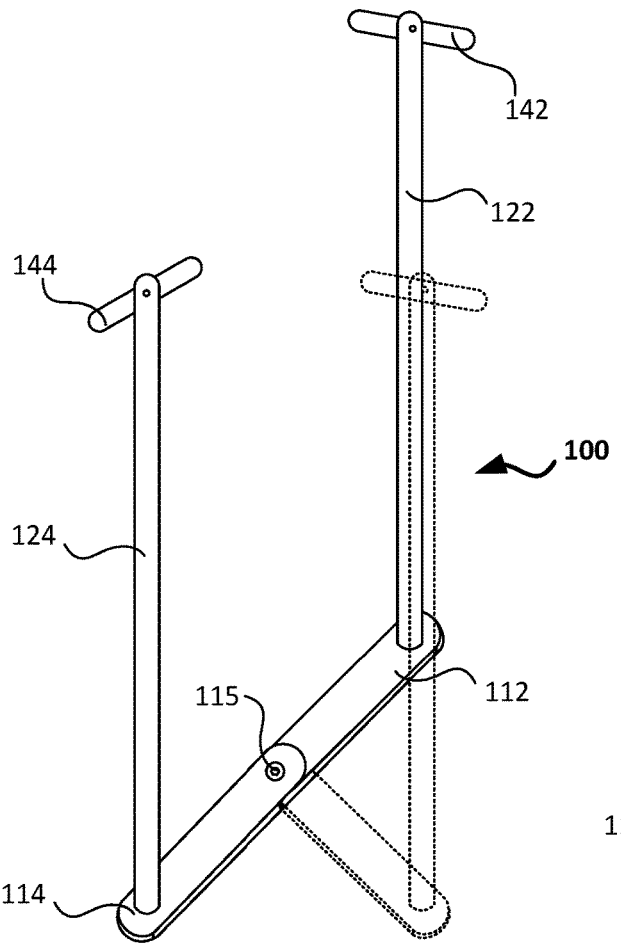
FIG. 8
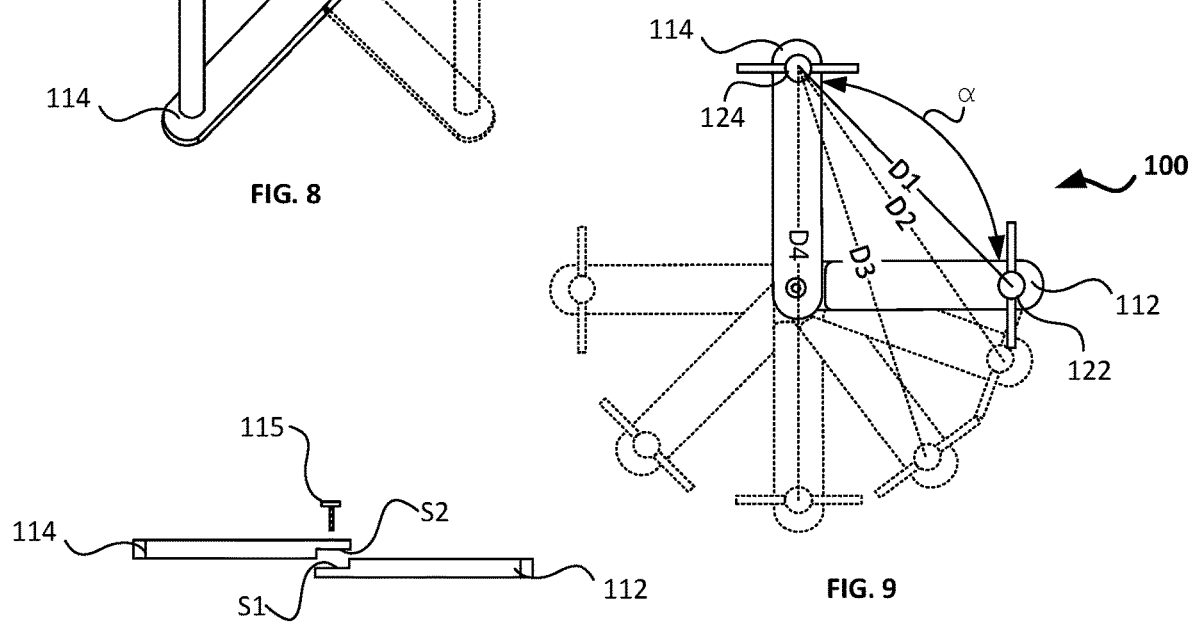
FIG. 9
FIG. 10

SURGICAL STRINGER AND METHODS OF MANUFACTURING AND USING SAME

CROSS-REFERENCE TO RELATED APPLICATIONS

The present application is a continuation of U.S. patent application Ser. No. 16/370,931, filed Mar. 30, 2019, the content of which is hereby incorporated by reference in its entirety as if fully set forth herein.

FIELD OF THE DISCLOSURE

The present disclosure relates to surgical stringers for use in medical settings. More particularly the present disclosure relates to adjustable surgical stringers capable of standing upright.

BACKGROUND OF THE DISCLOSURE

Surgical procedures regularly use sets of pre-selected surgical instruments for a specified surgical procedure, such as clamps, forceps, scissors, retractors, and the like. These instruments are regularly grouped together to form a set. The set of surgical instruments is stored in a sterilized condition until required for surgery. Prior to sterilization the set of surgical instruments is subject to a multi-step sorting, identifying, grouping, cleaning and sterilization process.

Typically, the set of surgical instruments is collected post operation, co-mingled in a wire mesh basket or holed tray for transport to the central sterile processing area. Next, the basket or tray of surgical instruments is placed in a wash sink to brush and manually wash the surgical instruments to remove any foreign debris, such as tissue or dried body fluid. The basket or tray of surgical instruments may then be transported to and run through an automated washer/decontaminator. Next, the basket or tray of surgical instruments is transported to and emptied out on a sorting table where a technician inspects, counts and sorts each surgical instrument into groupings of instruments for a specified surgical procedure. Pivoting or hinged scissor-like surgical instruments are commonly sequentially grouped using a fixed stringer positioned through both of the finger rings or ring handles, and the set is laid or positioned in a basket or tray. This basket or tray of surgical instruments is placed in a sealed container and sealed before entering the sterilization machine.

Traditional stringers are U-shaped members incapable of adjustability. Additionally, these U-shaped members are laid flat on a table, which makes the sorting, loading and collecting of the instruments difficult.

SUMMARY OF THE DISCLOSURE

In some embodiments, a surgical stringer includes a pair of bases, each of the pair of bases having a flat bottom surface, a pivot coupling the pair of bases together about the pivot, the pair of bases being rotatable with respect to one another, and a pair of poles, each of the pair of poles being coupled to one of the pair of bases and extending orthogonally thereto, the distance between the pair of poles being variable.

A method of storing surgical instruments includes providing a surgical stringer including a pair of bases, each of the pair of bases having a flat bottom surface, a pivot coupling the pair of bases together, the pair of bases being rotatable with respect to one another, and a pair of poles, each of the pair of poles having a keeper and being coupled to one of the pair of bases and extending orthogonally thereto, the distance between the pair of poles being variable, and sliding a first instrument over at least one of the keepers and the respective one of the pair of poles.

BRIEF DESCRIPTION OF THE DISCLOSURE

Various embodiments of the presently disclosed stringers are described herein with reference to the drawings, wherein:

FIG. 1 is a schematic perspective view of a surgical stringer according to one embodiment of the present disclosure;

FIGS. 2 and 3 are schematic bottom and top views of the surgical stringer of FIG. 1, respectively;

FIGS. 8 and 9 are schematic perspective and top views of the surgical stringer of FIG. 1 being disposed in various positions to adjust the distance between poles, respectively; and FIG. 10 is a schematic side view of a pair of bases that form the platform similar to that of FIG. 1.

Figure 4:
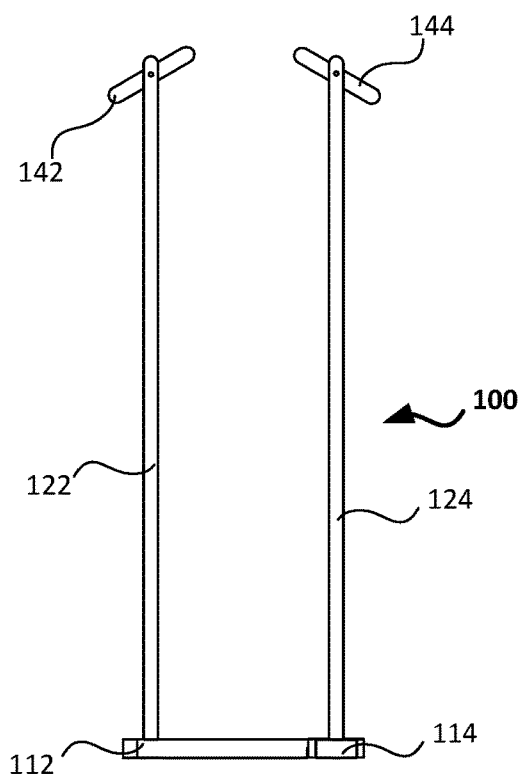
FIGS. 4-7 are schematic front, back, and side views of the surgical stringer of FIG. 1, respectively.
Figure 5:
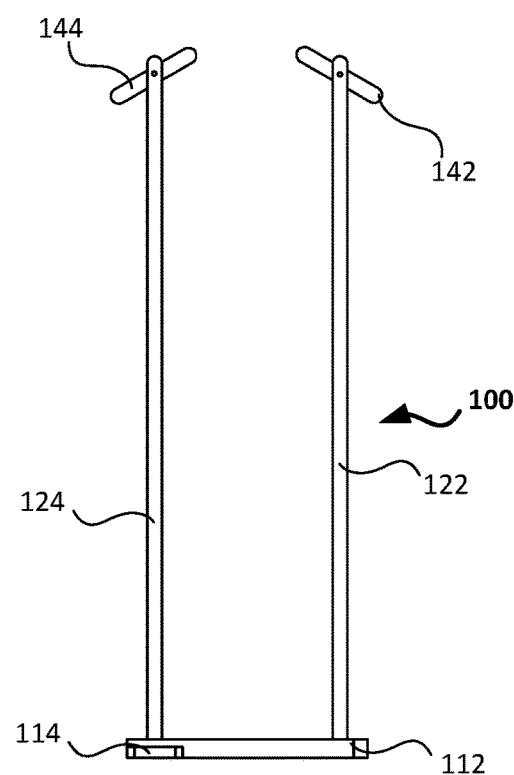
Figure 6:
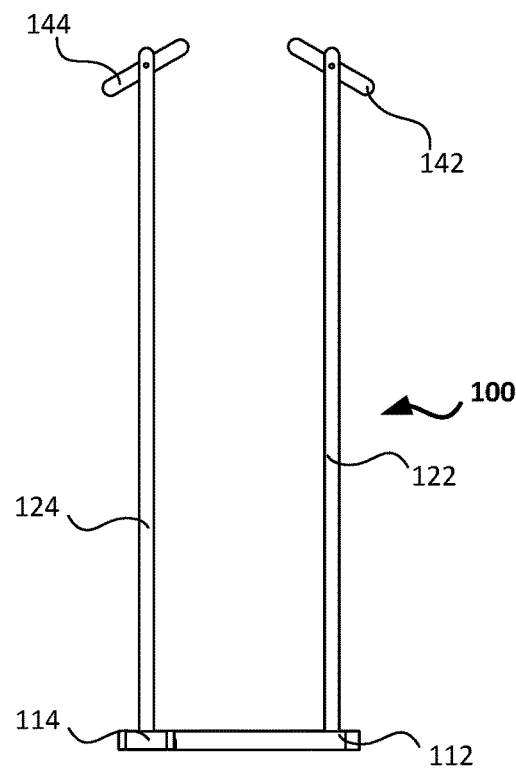
Figure 7:
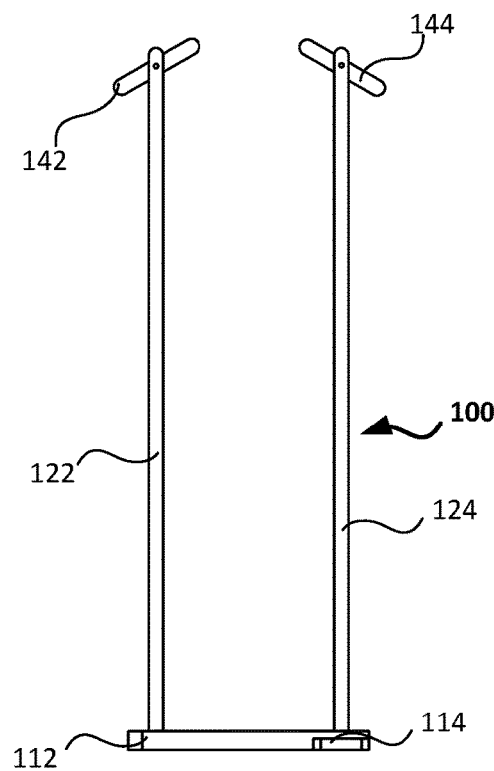

Various embodiments of the present invention will now be described with reference to the appended drawings. It is to be appreciated that these drawings depict only some embodiments of the invention and are therefore not to be considered limiting of its scope.

DETAILED DESCRIPTION

Despite the various improvements that have been made to surgical stringers, conventional devices suffer from some shortcomings as described above.

There therefore is a need for further improvements to the devices, systems, and methods of manufacturing and using stringers. Among other advantages, the present disclosure may address one or more of these needs.

As used herein, the term "proximal," when used in connection with a component of a stringer, refers to the end of the component closest to the platform, whereas the term "distal," when used in connection with a component of a stringer, refers to the end of the component farthest from the platform of the stringer.

FIG. 1 illustrates a perspective view of a surgical stringer 100 extending between a proximal end 102 and a distal end 104. Stringer 100 generally includes a platform 110 formed of a first base 112 and a second base 114, the two bases being operatively coupled together via a pivot 115. Pivot 115 may be in the form of a rivet, snap, stud, bolt, screw, pin or other suitable fastener that allows to members to rotate relative to one another.

In at least some examples, first base 112 and second base 114 may be formed of stainless steel, aluminum, metal, metal alloys, shape memory alloys, carbon fibers, nylon, ceramic or the like, capable of providing structure whether as a solid or hollow. Preferably, the material includes other suitable characteristics, such as durability, rigidity, stain-resistance, bacteria-resistance, light weight, chemical inertness, oxidation resistance, ease of workability, or other beneficial characteristic understood by one skilled in the art.

Each of first base 112 and second base 114 may have a flat upper surface facing the distal end 104, and a flat bottom surface facing the proximal end 102. Flat bottom surface is capable of lying flat to allow the stringer to stand upright on a table or other surface. Each of first base 112 and second base 114 may be ½ to 3 inches in width and 2 to 8 inches in length. As best shown in FIG. 10, each of bases 112, 114 may have a step S1, S2 formed of a thinned portion where the height of the base is approximately ½ of the height at the other end of the base or the remainder of the base (e.g., any part of the base that does not form the step), so that the two bases mate with each other at the steps S1, S2, a pivot 115 securing the two bases together and allowing the bases to rotate relative to one another about the pivot. The pivot may extend through each of the bases at the stepped portion.

A first arm or pole 122 is coupled to first base 112 and extends orthogonally relative thereto. The first pole 112 may be disposed on an end of the base opposite the pivot 115 and may be spaced halfway across the width of the first base 112 (See, FIG. 3). Likewise, a second pole 124 is coupled to the second base 114 and extends orthogonally relative thereto. The second pole 124 may be disposed on an end of the second base opposite the pivot 115 and may be spaced halfway across the width of the second base 114. Each of the poles 122, 124 may be formed as substantially cylindrical solid or hollow rods formed of the same or similar materials as bases 112, 114. In at least some examples, poles 122, 124 may be between 6" and 20" in length, the length of the poles being useful to accommodate more or less instruments.

At a distal end 104 of stringer 100 are pins 132, 134 connected to the distal end of each poles 122, 124 respectively, the pins 132, 134 being capable of connecting keepers 142, 144 to the poles as shown. Keepers 142, 144 may be relatively thin and flat components made of a metal (e.g., stainless steel) or other suitable material that are capable of rotating about pins 132, 134 as shown in FIG. 1, so that the keepers may be aligned with axis of the poles as annotated by position K1, and off-axis with the poles as shown in positions K2, K3. Each keeper may have an open condition and a closed condition. When the keepers 142, 143 are in the vertical position and aligned with the longitudinal axis of the poles 122, 124, an instrument may be slipped over the keepers and down the length of the poles. Alternatively, after the instruments have been slid onto the poles, keepers 142, 143 may be rotated into non-vertical positions, such as K2, K3, thereby effectively securing the instruments within the stringer and preventing them from falling off of the stringer.

As shown in FIGS. 8 and 9, first and second base 112, 114 may rotate around pivot 115 to define an angle α therebetween. In at least some examples, first and second bases 112, 114 may define an angle α of 90 degrees, 180 degrees or any angle within that range (e.g., 110 degrees or 135 degrees). Additionally, it will be understood that one of the bases may swing fully around to form an angle on either side of the other base so that the bases have a range of motion of 270 degrees relative to one another. By varying the angle α that is formed between the two bases 112, 114, the distance between the two poles 122, 114 may also be changed as shown with the rotation of base 112 shown in phantom lines.

Specifically, the distance between the poles 122, 124 may vary between distance D1 defined as the distance between the two poles 122, 124 when the two bases are orthogonal with one another, and distance D4 defined as the distance between poles 122, 124 when the two bases are in-line with one another. Various other distances (e.g., distances D2, D3, etc.) are also possible at other angles α. In least some examples, the distance between poles 122, 124 may vary between 2 inches and 9 inches. In least some examples, the distance between poles 122, 124 may vary between 3 inches and 6 inches. In this way, stringer 100 may be used to accommodate instruments of different sizes by adjusting the angle between bases, and with it the distance between poles.

In use, a stringer may be used to load a number of instruments for sterilization. The stringer may be disposed upright on the flat wide lower surfaces of the bases that form the platform, the stringer being capable of standing upright without any external support. The angle of the bases may be adjusted and selected based on the intended use, so that the angle is anywhere between 90 and 180 degrees. For example, for larger instruments, the distance between the poles may be increased by rotating one of the bases relative to the other to form a larger angle. To load the instruments, the keepers 142, 144 may be vertically disposed and handles or loops in the instruments may be slid onto the poles from the top, through the keepers and down toward the base. Additional instruments may be loaded as necessary. Once all the instruments are loaded, the keepers 142, 144 may be rotated to a horizontal or angled position with respect to the poles, securing the instruments over the poles between the keeper and the respective base. The loaded stringer may then be sent for sterilization. To unload the stringer, the stringer may be set up vertically on a table or other surface, the keepers may be rotated to the vertical position, and the instruments may be removed one at a time.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

What is claimed is:

1. A surgical stringer comprising:
   a pair of bases, each of the pair of bases having a flat bottom surface, the pair of bases being moveable relative to one another;
   a pair of poles, each of the pair of poles being coupled to one of the pair of bases and extending orthogonally thereto, the distance between the pair of poles being variable; and
   a keeper disposed on an end of each of the pair of poles, the keeper being transitionable between an open position that allows an instrument handle to slide therethrough onto the corresponding pole in a first orientation and a closed position to secure the instrument handle on the corresponding pole in a second orientation.

2. The surgical stringer of claim 1, wherein the distance between the pair of poles is proportional to an angle between the pair of bases.

3. The surgical stringer of claim 1, wherein the pair of bases may form an angle of between 90 degrees and 180 degrees relative to one another.

4. The surgical stringer of claim 1, further comprising a keeper disposed on an end of each of the poles.

5. The surgical stringer of claim 4, wherein the keeper is rotatable with respect to a respective pole.

6. The surgical stringer of claim 1, wherein the pair of bases and the pair of poles comprise a same material.

7. The surgical stringer of claim 1, wherein the pair of bases and the pair of poles are metallic.

8. The surgical stringer of claim 1, wherein each of the pair of bases includes a first height and a thinned step portion.

9. The surgical stringer of claim 8, wherein the thinned step portion is approximately ½ of the first height.

10. The surgical stringer of claim 8, wherein the pair of bases mate with one another at respective thinned step portions.

11. The surgical stringer of claim 8, further comprising a pivot extending through the thinned step portion of each of the pair of bases.

12. The surgical stringer of claim 1, wherein the distance between the pair of poles may be selected to be between 2 inches and 9 inches by changing an angle formed between the pair of bases.

13. A method of storing surgical instruments comprising:
providing a surgical stringer including a pair of bases, each of the pair of bases having a flat bottom surface and being moveable relative another of the pair of bases, and a pair of poles, each of the pair of poles having a keeper disposed on an end of each of the pair of poles, the keeper being transitionable between an open position that allows an instrument handle to slide therethrough onto the corresponding pole in a first orientation and a closed position to secure the instrument handle on the corresponding pole in a second orientation, and being coupled to one of the pair of bases and extending orthogonally thereto, the distance between the pair of poles being variable; and
sliding a first instrument over at least one of the keepers and the respective one of the pair of poles.

14. The method of claim 13, further comprising the step of transitioning the keeper between an open position and a closed position.

15. The method of claim 13, further comprising the step of standing the surgical instrument upright on the flat bottom surface so that the poles extend upward toward a user.

16. The method of claim 13, further comprising the step of rotating one of the pair of bases relative to another to a desired angle.

17. The method of claim 16, wherein rotating one of the pair of bases relative to another varies the distance between the pair of poles.

18. The method of claim 17, wherein rotating one of the pair of bases relative to another includes forming an angle of between 90 degrees of 180 degrees between the pair of bases.

19. The method of claim 13, wherein providing a surgical instrument includes providing a pair of bases, each of the pair of bases having a first height and a thinned step portion, the thinned step portions of the pair of bases mating with each other adjacent a pivot.

* * * * *